United States Patent [19]

Yasui et al.

[11] 4,377,691

[45] Mar. 22, 1983

[54] PROCESS FOR THE PREPARATION OF 1-(4-HYDROXYPHENYL)-2-(4-BENZYL-PIPERIDINO)-1-PROPANOL AND ACID-ADDITION SALTS THEREOF

[75] Inventors: Bompei Yasui, Ikoma; Tomohisa Miyamoto, Settsu; Katsuyuki Hiraoka, Neyagawa; Yoshitaka Sako, Osaka, all of Japan

[73] Assignee: Kabushiki Kaisha Cosmos Enterprise, Osaka, Japan

[21] Appl. No.: 213,033

[22] Filed: Dec. 4, 1980

[30] Foreign Application Priority Data

Dec. 7, 1979 [JP] Japan ................................ 54-158112
Dec. 30, 1979 [JP] Japan ................................ 54-173198
Mar. 27, 1980 [JP] Japan ................................ 55-38228
Mar. 27, 1980 [JP] Japan ................................ 55-38229

[51] Int. Cl.$^3$ ........................................ C07D 211/14
[52] U.S. Cl. .................................... 546/185; 546/240; 546/340
[58] Field of Search ................. 546/185, 240, 340

[56] References Cited

U.S. PATENT DOCUMENTS 2,695,919  11/1954  Wright et al. ........................ 546/240
3,509,164   4/1970  Carron et al. ........................ 546/240

FOREIGN PATENT DOCUMENTS 47-15348  5/1972  Japan.
50-4081   1/1975  Japan.

OTHER PUBLICATIONS

Chemische Berichte, vol. 86, No. 12, (1953), pp. 1556–1558.
A. V. Dombrovskii et al., Jour. Gen. Chem. USSR, vol. 32, (1962), pp. 2246–2248.
S. J. Pasaribu et al., Aus. J. Chem., vol. 26, (1973), pp. 1327–1331.
Alan E. Ardis et al., Jour. Am. Chem. Soc., vol. 68, (1946), pp. 591–595.

*Primary Examiner*—Norma S. Milestone
*Attorney, Agent, or Firm*—Birch, Stewart, Kolasch & Birch

[57] ABSTRACT

A process for the preparation of 1-(4-hydroxyphenyl)-2-(4-benzylpiperidino)-1-propanol (i.e. ifenprodil) and acid-addition salts thereof, characterized by brominating 4'-hydroxypropiophenone in a single or mixed solvent selected from the group consisting of methanol, ethanol and a saturated aliphatic ether, removing hydrogen bromide formed in the course of the bromination, adding 4-benzylpyridine to the reaction mixture, heating the reaction mixture under reflux in a single or mixed solvent selected from the group consisting of methanol and ethanol, and then subjecting the resultant reaction mixture to catalytic reduction to form 1-(4-hydroxyphenyl)-2-(4-benzylpiperidino)-1-propanol hydrobromide in the reaction mixture. The end product (i.e. ifenprodil) can be obtained according to this process in a high yield of about 80% within 14 hours from the starting material in a single reaction container throughout the process, without introducing a protective benzyl group into the starting material prior to the bromination.

17 Claims, No Drawings

PROCESS FOR THE PREPARATION OF 1-(4-HYDROXYPHENYL)-2-(4-BENZYL-PIPERIDINO)-1-PROPANOL AND ACID-ADDITION SALTS THEREOF

BACKGROUND OF THE INVENTION

1. Field of the Invention

The present invention relates to a new valuable process for the preparation of 1-(4-hydroxyphenyl)-2-(4-benzylpiperidino)-1-propanol and acid-addition salts thereof. This compound is called ifenprodil and is useful as a therapeutic agent for the treatment of cerebrovascular diseases.

2. Description of the Prior Art 1-(4-Hydroxyphenyl)-2-(4-benzylpiperidino)-1-propanol which is referred to hereinafter as ifenprodil is known and is represented by the structural formula:

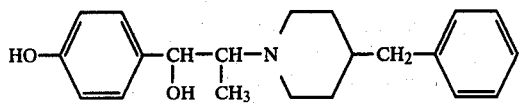

All the processes known hitherto for preparing ifenprodil produce α-bromo-4'-benzyloxypropiophenone as an intermediate product (e.g. Japanese Patent Publn. No. 15348/72 and Japanese Laid-open Patent Appln. No. 4081/75). According to these prior art processes wherein 4'-hydroxypropiophenone is used as the main starting material, ifenprodil is prepared only by passing through the steps of benzylating the starting material to form 4'-benzyloxypropiophenone and then brominating the latter to obtain α-bromo-4'-benzyloxypriophenone. The benzyloxy group formed in the 4-position of the phenyl ring by the benzylation prior to the bromination is after all debenzylated in the posterior step so that the 4-position is again occupied by the hydroxyl group in ifenprodil which is the objective product of the reaction. The reason why such benzylation, which rather seems to be unnecessary, has to be carried out in the 4-position prior to the bromination is that when 4'-hydroxypropiophenone is directly subjected to bromination, the bromine-substitution tends to take place rather easily on the phenyl ring, thus making it difficult to attain the desired bromine-substitution in the α-position. However, the benzyloxy group in 4'-benzyloxypropiophenone formed as an intermediate is after all to be converted into the hydroxy group before obtaining ifenprodil, the end product. To say it in another way, the hydroxy group in the starting 4'-hydroxypropiophenone is once converted by the benzylation into the benzyloxy group for the purpose of protecting the phenyl ring from any ring-bromination and the protective benzyl group once introduced has to be split off before obtaining ifenprodil.

If elimination of such temporarily protecting steps for introducing and removing the benzyl group is possible in the preparation of ifenprodil from 4'-hydroxypropiophenone, it will apparently bring about outstanding advantages in the efficiency of a procedure for preparing ifenprodil. Heretofore, however, no study has been reported on the elimination of such protecting steps in the prior art processes for preparing ifenprodil.

Thus, there is still a great demand in this art for developing a new process which can obviate the disadvantages of the prior art processes and by which ifenprodil can be prepared in a high yield by a simple and economical means.

BRIEF SUMMARY OF THE INVENTION

Accordingly, it is an object of the present invention to provide a new process for the preparation of ifenprodil wherein drawbacks in the prior art processes are obviated.

It is another object of the present invention to provide a new advantageous process for the preparation of ifenprodil wherein the benzylation prior to the bromination for the purpose of temporary protection can be omitted.

It is still another object of the present invention to provide a new efficient process for the preparation of ifenprodil wherein all of the steps can be carried out in a single reaction container.

It is further object of the present invention to provide an economical process for the preparation of ifenprodil wherein the reduction step can be conducted without heating under ambient pressure.

Other objects, features and advantages of the present invention will become apparent more fully from the following description.

DETAILED DESCRIPTION OF THE INVENTION

As a result of extensive researches made for developing a new valuable process for the preparation of ifenprodil in a high yield without effecting the inconvenient benzylation, it has now been found surprisingly that ifenprodil of high quality can be prepared in a high yield without performing the benzylation step by conducting the α-bromination and the subsequent steps under specifically selected reaction conditions. The present invention has been accomplished on the basis of the above finding.

In accordance with the present invention, there is provided a process for the preparation of ifenprodil [i.e. 1-(4-hydroxyphenyl)-2-(4-benzylpiperidino)-1-propanol] and acid-addition salts thereof, characterized by brominating 4'-hydroxypropiophenone in a single or mixed solvent selected from the group consisting of methanol, ethanol and a saturated aliphatic ether, removing hydrogen bromide formed in the course of the bromination, adding 4-benzylpyridine to the reaction mixture, heating the reaction mixture under reflux in a single or mixed solvent selected from the group consisting of methanol and ethanol and then subjecting the resultant reaction mixture to catalytic reduction to form ifenprodil hydrobromide in the reaction mixture.

In the initial bromination step wherein 4'-hydroxypropiophenone is directly used as the main starting material, the reaction solvent is selected from the group of methanol, ethanol and a saturated aliphatic ether. The reaction solvent may be any of these solvents or a mixed solvent of at least two of these. The saturated aliphatic ether involves not only a usual lower saturated aliphatic ether but also an alicyclic ether. Illustrative of the saturated aliphatic ether are, for example, lower alkyl ethers such as diethyl ether, di-n-propyl ether and di-n-butyl ether, and alicyclic ethers such as dioxane and tetrahydrofuran. The reason why the reaction solvent in the bromination step is to be limited to one or more of these solvents is that the use of these solvents permits no ring-bromination and serves to effect bromination exclusively in the α-position of the starting 4'-hydroxypropiophenone.

In the bromination step, the use of dioxane is preferable as the ethereal solvent. The use of methanol or ethanol is also convenient since the solvent used in the subsequent steps, i.e. condensation with 4-benzylpyridine and catalytic reduction of the resultant condensation product, is limited to methanol and/or ethanol. The amount of the solvent can be varied within a wide range and the minimum amount of the solvent used depends on its ability of solubilizing 4'-hydroxypropiophenone. In case the ethereal solvent such as dioxane or tetrahydrofuran is used alone or as a mixture with methanol and/or ethanol in the bromination step, the amount of such ethereal solvent is carefully chosen lest the reactions in the subsequent steps should be disturbed by the coexistence of such ethereal solvent in methanol and/or ethanol used as the solvent in the subsequent steps. In case of dioxane, for example, 0.6–1.0 part by volume is usually used per part by weight of 4'-hydroxypropiophenone.

Any of the brominating agents usually employed for bromination reactions, such as bromine, phosphorus pentabromide or the like, may be used in the bromination step of the present invention. The use of bromine itself is preferable. The brominating agent is used in an almost theoretical amount with respect to the starting 4'-hydroxypropiophenone. For example, bromine can be used in an amount up to a slight excess over the stoichiometric amount but the use of a large excess amount of bromine is to be avoided.

The bromination reaction is carried out by adding 4'-hydroxypropiophenone to a given amount of the solvent and dropping bromine into the mixture. The desired bromination in the α-position is promoted usually at room temperature without necessity of any catalyst or irradiation of actinic light which may rather serve to cause undesirable ring-bromination. The bromination is completed usually within the period of 10–30 minutes. The reaction mixture may be stirred for an additional 5–15 minutes at room temperature.

As the bromination reaction proceeds, α-bromo-4'-hydroxypropiophenone is formed in the reaction mixture and at the same time hydrogen bromide is evolved in an equimolar amount with the above brominated product. It has been found by the present inventors that the condensation reaction in the successive step wherein α(or 2)-bromo-4'-hydroxypropiophenone is reacted with 4-benzylpyridine can smoothly be promoted by removing the hydrogen bromide formed as by-product and existing in the brominated reaction mixture according to the specific two alternative methods.

In an embodiment of the step of removing the hydrogen bromide, a basic substance is used to fix the hydrogen bromide as a salt in the reaction system. This embodiment proceeds according to the mode of an ordinary neutralization of an acid with a base. Examples of the basic substance include, in addition to 4-benzylpyridine itself used in the next condensation step, organic and inorganic weakly basic substances such as potassium hydrogen carbonate, sodium hydrogen carbonate, potassium carbonate, sodium carbonate, sodium acetate, magnesium hydroxide, triethylamine and the like tertiary amine; and organic and inorganic strongly basic substances such as sodium hydroxide, potassium hydroxide and trimethylammonium hydroxide. The use of an alkali metal hydrogen carbonate such as potassium hydrogen carbonate and caustic alkali such as sodium hydroxide is advantageous. The amount of the basic substance is approximately stoichiometric with respect to the hydrogen bromide formed in the reaction system. The existence of an excess amount of the basic substance in the reaction system does not give any adverse influence on the condensation reaction in the subsequent step. However, care should be taken with respect to the amount of the basic substance because the presence of a basic substance in the reaction system will give a harmful effect on the catalytic reduction subsequent to the condensation reaction.

In case a strongly basic substance such as sodium hydroxide is used, care should particularly be taken to the point that the amount of such strongly basic substance should not be stoichiometrically in excess. For example, the amount of such strongly basic substance should not exceed 1 molar proportion, even if 1 molar proportion of 4'-hydroxypropiophenone is reacted with 1 molar proportion of bromine, taking such situation into consideration that a part of the hydrogen bromide formed as by-product may escape in the form of a gas from the reaction system.

The embodiment itself wherein the hydrogen bromide is removed by fixing it with the basic substance in the reaction system is carried out by adding the basic substance to the reaction mixture obtained in the bromination step. However, this embodiment may advantageously be carried out simultaneously with the next condensation step. In this case, methanol and/or ethanol is added together with 2 molar proportion of 4-benzylpyridine or with 1 molar proportion of 4-benzylpyridine and 1 molar proportion of the weakly basic substance such as potassium hydrogen carbonate or 0.7 molar proportion of the strongly basic substance such as sodium hydroxide to the reaction product obtained in the preceding bromination step by reacting 1 molar proportion of 4'-hydroxypropiophenone with 1 molar proportion of bromine. If desired, a small amount of water is added to the mixture and the whole is heated under reflux. In this preferable embodiment, the hydrogen bromide formed as by-product in the bromination step is neutralized with the basic substance and the condensation of the brominated compound with 4-benzylpyridine is promoted smoothly. In this embodiment, a salt formed by neutralization of hydrogen bromide with the basic substance is present in the reaction system. It has been found, however, that the presence of such salt does not give any adverse influence on the catalytic reduction in the subsequent step.

In another embodiment of the step for removing the hydrogen bromide formed as by-product in the bromination step, an inert gas is introduced into the reaction mixture after the bromination to expel the gaseous hydrogen bromide together with the inert gas. Preferable examples of the inert gas include air and nitrogen. In this embodiment, a stream of such inert gas is preferably supplied from a pressurized tank and introduced continuously at a proper flow rate into the reaction mixture. No special limitation is set for the flow rate and the period of time for introducing the inert gas, but a flow rate of 100–500 ml/minute and an introduction time of 10–40 minutes are usually employed in a suitable combination. In this case, the temperature of the reaction system is usually maintained from room temperature to about 60° C. The hydrogen bromide expelled from the reaction system in the form entrained in the inert gas can easily be captured by way of a water trap or the like absorbing medium. Unlike the firstly mentioned embodiment wherein the hydrogen bromide is removed from the reaction system by neutralization with the basic substance, this embodiment is necessarily carried out prior to the condensation step.

After removal of the hydrogen bromide is finished by either of the above alternative embodiments, 4-benzylpyridine and methanol (and/or ethanol) are added to the reaction mixture and the condensation step is carried out by heating the mixture under reflux. The amount of 4-benzylpyridine to be added is at least equimolar, preferably 1-1.2 molar proportion to the starting 4'-hydroxypropiophenone.

As one of the gists of this invention resides in the use of a single reaction container throughout all of the steps, the amount of the solvent used in the initial bromination step is as small as possible and an additional solvent or solvents are used in the subsequent condensation and reduction steps. In case methanol and/or ethanol is used in the bromination step, an additional amount of the same solvent is used in the condensation and reduction steps. In case the ethereal solvent alone is used in the bromination step, however, methanol and/or ethanol is newly added on performance of the condensation and reduction steps. In the condensation step, methanol and/or ethanol is added preferably in an amount of 500-3000 ml per mol of the starting 4'-hydroxypropiophenone. The solvent used or to be added in the condensation step should secure, on reflux of the reaction mixture, a temperature high enough to promote the condensation reaction smoothly. Thus, the solvent used should have a boiling point which, on reflux of the reaction mixture, affords such reaction temperature. In addition, the solvent used is preferably one which ensures smooth proceeding of the subsequent reactions. In case the condensation product formed in this step is subjected to the subsequent catalytic reduction step, it is desirable that the condensation product is present in the reaction system in a dissolved state in the reaction liquid to ensure smooth proceeding of the reduction of the condensation product. Methanol and ethanol have boiling points high enough to promote the condensation reaction on reflux of the reaction mixture and high solubilizing power for the condensation product to be reduced. Thus, the solvent used in the condensation and reduction steps is limited to methanol and ethanol.

In the condensation step, the condensation reaction between 2-bromo-4'-hydroxypropiophenone and 4-benzylpyridine is smoothly promoted in the presence of methanol and/or ethanol whereby a ketone compound of the general formula:

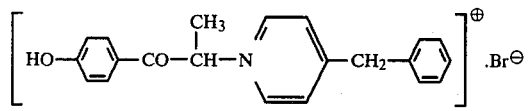

i.e. 4-benzyl-1-[1-(4-hydroxyphenylcarbonyl)ethyl]-pyridinium bromide is formed in the reaction mixture. The time and the temperature adopted for the condensation reaction are usually 3-6 hours and 60°-90° C., respectively. The reaction mixture thus obtained is directly subjected as such, without isolating the above condensation product, to the catalytic reduction in the subsequent step. In this case, an additional amount of methanol and/or ethanol may be supplied to the reaction mixture.

The catalytic reduction reaction in the next reduction step is carried out in one embodiment by adding a hydrogenation catalyst to the reaction mixture obtained in the preceding condensation step and treating the mixture with hydrogen under ordinary hydrogenating conditions, for example, under a pressure of 15-60 kg/cm$^2$ at 50°-95° C. over the period of 5-9 hours, or in another more advantageous embodiment by adding platinum oxide to the reaction mixture obtained in the preceding condensation step and treating the mixture with hydrogen under atmospheric pressure without heating for the period of 6-13 hours, preferably 7-12 hours.

Examples of the hydrogenation catalyst used in the firstly mentioned embodiment include palladium-carbon, Raney metals such as Raney nickel and Raney cobalt, rhodium-carbon and copper chromite catalysts. In the firstly mentioned embodiment, the catalytic reduction reaction proceeds under the above mentioned conditions (at an elevated temperature under pressure). According to the present inventors' study, however, it has been found that the reaction does not proceed smoothly if either or both of the temperature and pressure conditions is outside the described range. Accordingly, it is quite unexpected that the catalytic reduction reaction can be promoted smoothly without the necessity of heating and pressurizing in the secondly mentioned embodiment wherein platinum oxide is used which is similar to other hydrogenation catalysts.

In the reduction step, 4-benzyl-1-[1-(4-hydroxyphenylcarbonyl) ethyl]-pyridinium bromide existing in the reaction mixture obtained in the preceding condensation step is catalytically reduced whereby ifenprodil hydrobromide is obtained in a good yield. The catalytic reduction itself is conducted in the manner known per se under given conditions. After completion of the catalytic reduction reaction, solid matters including the hydrogenation catalyst are removed by filtration from the reaction mixture and the filtrate is concentrated, if necessary, under reduced pressure. Crude ifenprodil hydrobromide can then be crystallized out by adding, if desired, water or an organic solvent to the residue or by directly cooling the residue. The crude product thus obtained is purified in a usual manner by recrystallization from an organic solvent such as ethanol or is treated with a theoretical amount of an alkaline substance such as sodium hydroxide or ammonia water whereby the free ifenprodil can be obtained.

In the practical preparation of the free ifenprodil, it is convenient to obtain the free ifenprodil directly from the reaction mixture, without once isolating ifenprodil hydrobromide, by adding ammonia water or a similar weakly basic substance to the filtrate from which solid matters including the catalyst have been removed, and concentrating the filtrate under reduced pressure to obtain the free compound as a residue which may, if desired, be purified by recrystallization from ethanol or isopropanol. The filtrate or mother liquor in the crystallization and/or recrystallization treatment may be subjected to silica gel column chromatography to recover a certain amount of ifenprodil. The total yields of ifenprodil can be increased by this after-treatment to about more than 90%. The free ifenprodil thus obtained may be reacted with an acid in a proper solvent to prepare an acid-addition salt with the acid.

The process of this invention is particularly advantageous as an industrial process for preparing ifenprodil and exhibits the following remarkable merits:

(1) In the process of this invention, benzylation of the 4'-hydroxy group as adopted in the prior art processes for protecting the phenyl ring from bromination is not performed at all so that the work efficiency for preparation of the end product can be enhanced significantly as compared with the prior art processes wherein introduction and removal of the benzyl group is indispensable for preventing side reactions. Thus, the yield of the end product can extremely be increased in the present invention.

(2) As an incidental advantage resulting from omission of the preliminary benzylation step as required in the prior art processes, the problem of handling a harmful substance such as benzyl chloride as the reactant for the introduction of a benzyl group is eliminated.

(3) In the process of this invention, all of the steps beginning with the bromination of 4'-hydroxypropiophenone and ending with the catalytic reduction of 1-[1-(4-hydroxyphenylcarbonyl)ethyl]pyridinium bromide can be conducted in a single reaction container, without isolating the intermediate bromine products which are generally harmful in handling and the operation can be conducted with a high efficiency.

(4) According to the advantageous embodiment of the catalytic reduction wherein platinum oxide is used as a hydrogenation catalyst, the reduction reaction can be promoted without necessity of heating and pressurizing the reaction container so that the present invention is more advantageous in facilities, efficiency and safety of work and investment of capital than the prior art processes wherein heating and pressurizing of the reaction container are necessary.

In view of these technical merits, the present invention is very superior in the yield of the end product, shortening of working time and overall efficiency of the work needed for preparing the end product to any of the known prior art processes. For example, it is possible according to the present invention to prepare ifenprodil in a high yield of about 80% within 14 hours, starting from 4'-hydroxypropiophenone. On the other hand, the total working time required for preparing ifenprodil according to the process disclosed in Japanese Laid-open Patent Appln. No. 4081/75 is 26–78 hours (3–8 hours for the condensation reaction and 23–70 hours for the reduction reaction) and the yield of ifenprodil is about 75% in average, even starting from the brominated compound. This comparison demonstrates the significant advantages of the present invention in combination of the working time and the yield.

The present invention will now be illustrated in more detail by way of examples.

EXAMPLE 1

To 4 ml of dioxane were added 6.0 g of 4'-hydroxypropiophenone. 6.4 Grams of bromine were added dropwise to the mixture with stirring at room temperature. The reaction liquid was stirred for an additional 10 minutes and then air was introduced thereinto at a flow rate of 400 ml/minute for 15 minutes at 60° C. To the reaction liquid were then added 7.5 g of 4-benzylpyridine and 50 ml of methanol, and the mixture was refluxed under heating for 5 hours. After replacing the air in the reaction container with nitrogen, 2.0 g of 10% palladium-carbon were added and hydrogen gas was then introduced and the mixture was stirred for 8 hours at 90°–95° C. under pressure of 50 kg/cm². After completion of the reaction, solid matters including the catalyst were filtered off and 30 ml of 10% ammonia water were added to the filtrate and the reaction liquid was concentrated under reduced pressure until its volume became 20 ml. The residual oily substance was crystallized from a mixture of 15 ml of diethyl ether and 15 ml of petroleum ether under ice-cooling and the resultant crude product was recrystallized from isopropanol whereby 10.6 g (68.8%) of ifenprodil were obtained as white crystals. M.P. 109°–111° C.

TLC: Rf 0.35

Diatomaceous earth and chloroform-diethylamine (95:5) were used as the support and the developing solvent, respectively. On irradiation of ultra-violet rays and in a color reaction with Dragen-dorff reagent, a single spot was detected.

NMR absorption spectra (DMSO-$d_6$; δ ppm):

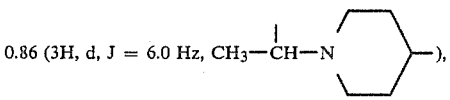

0.86 (3H, d, J = 6.0 Hz, CH₃—CH—N⟨⟩—),

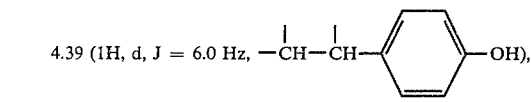

4.39 (1H, d, J = 6.0 Hz, —CH—CH—⟨⟩—OH), 6.47–7.00 (9H, m, aromatic ring protons)

Elementary analysis as $C_{21}H_{27}NO_2 \cdot C_3H_8O$: Calc.: C, 74.76%; H, 9.15%; N, 3.63%. Found: C, 74.66%; H, 9.10%; N, 3.55%.

EXAMPLE 2

To 4 ml of dioxane were added 6.0 g of 4'-hydroxypropiophenone. 6.4 Grams of bromine were added dropwise to the mixture with stirring at room temperature. The reaction liquid was stirred for an additional 5 minutes and then air was introduced thereinto at a flow rate of 200 ml/minute for 30 minutes at room temperature. To the reaction liquid were then added 7.5 g of 4-benzylpyridine and 50 ml of methanol, and the mixture was refluxed under heating for 5 hours. After replacing the air in the reaction container with nitrogen, 2.0 g of 10% palladium-carbon were added and hydrogen gas was then introduced and the mixture was stirred for 8 hours at 60°–70° C. under pressure of 50 kg/cm². After completion of the reaction, the catalyst and the like were filtered off and the filtrate was concentrated under reduced pressure until dryness. The residue was crystallized from acetone and the resultant crude product was recrystallized from ethanol whereby 14.9 g (92.0%) of ifenprodil hydrobromide were obtained as white crystals. M.P. 188°–191° C.

TLC: Rf 0.35

Diatomaceous earth and chloroform-diethylamine (95:5) were used as the support and the developing solvent, respectively. On irradiation of ultra-violet rays and in a color reaction with Dragendorff reagent, a single spot wes detected.

NMR absorption spectra (DMSO-$d_6$; δ ppm):

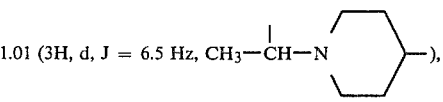

1.01 (3H, d, J = 6.5 Hz, CH₃—CH—N⟨⟩—),

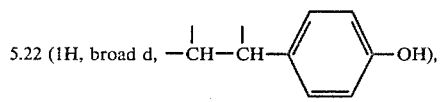

5.22 (1H, broad d, —CH—CH—⟨⟩—OH),

-continued
6.55–7.06 (9H, m, aromatic ring protons)

Elementary analysis: as $C_{21}H_{27}NO_2 \cdot HBr$: Calc: C, 62.07%; H, 6.94%; N, 3.45% Found: C, 62.11%; H, 6.96%; N, 3.43%

EXAMPLE 3

To 4 ml of dioxane were added 6.0 g of 4'-hydroxypropiophenone. 6.4 Grams of bromine were added dropwise to the mixture with stirring at room temperature. The reaction liquid was stirred for an additional 10 minutes and then nitrogen gas was introduced thereinto at a flow rate of 200 ml/minute for 30 minutes at room temperature. To the reaction liquid were then added 7.5 g of 4-benzylpyridine and 100 ml of ethanol, and the mixture was refluxed under heating for 3 hours. After replacing the air in the reaction container with nitrogen gas, 3.0 g of 5% palladium-carbon were added and hydrogen was then introduced and the mixture was stirred for 8 hours at 90°–95° C. under pressure of 50 kg/cm². After completion of the reaction, the reaction mixture was worked up in the same manner as described in Example 2 whereby 14.2 g (87.7%) of ifenprodil hydrobromide were obtained as white crystals.

The physical characteristics of these crystals were identical with those of the crystals obtained in Example 2.

EXAMPLE 4

To 4 ml of dioxane were added 6.0 g of 4'-hydroxypropiophenone. 6.4 Grams of bromine were added dropwise to the mixture with stirring at room temperature. The reaction liquid was stirred for an additional 10 minutes and then nitrogen gas was introduced thereinto at a flow rate of 200 ml/minute for 30 minutes at room temperature. To the reaction liquid was then added 6.4 g of 4-benzylpyridine and 50 ml of methanol, and the mixture was refluxed under heating for 5 hours. After replacing the air in the reaction container with nitrogen gas, 2.0 g of 10% palladium-carbon were added and hydrogen was then introduced and the mixture was stirred for 8 hours at 90°–95° C. under pressure of 20 kg/cm². After completion of the reaction, the reaction mixture was treated in the same manner as described in Example 2 whereby 10.6 g (65.2%) of ifenprodil hydrobromide were obtaind as white crystals.

The physical characteristics of these crystals were identical with those of the crystals obtained in Example 2.

EXAMPLE 5

To 4 ml of dioxane were added 6.0 g of 4'-hydroxypropiophenone. 6.4 Grams of bromine were added dropwise to the mixture with stirring at room temperature. The reaction liquid was stirred for an additional 10 minutes and then air was introduced thereinto at a flow rate of 400 ml/minute for 15 minutes at 60° C. To the reaction liquid were then added 7.5 g of 4-benzylpyridine and 50 ml of methanol, and the mixture was refluxed under heating for 5 hours. After replacing the air in the reaction container with nitrogen gas, 2.0 g of 10% palladium-carbon was added and hydrogen was then introduced and the mixture was then treated in the same manner as described in Example 3 whereby 15.3 g (94.4%) of ifenprodil hydrobromide were obtained as white crystals.

The physical characteristics of these crystals were identical with those of the crystals obtained in Example 2.

EXAMPLE 6

To 4 ml of dioxane were added 6.0 g of 4'-hydroxypropiophenone. 6.4 Grams of bromine were added dropwise to the mixture with stirring at room temperature. The reaction liquid was stirred for an additional 10 minutes and then nitrogen gas was introduced thereinto at a flow rate of 200 ml/minute for 30 minutes at room temperature. To the reaction liquid were then added 7.5 g of 4-benzylpyridine and 100 ml of ethanol, and the mixture was refluxed under heating for 5 hours. After replacing the air in the reaction container with nitrogen gas, 3.0 g of 10% palladium-carbon were added and hydrogen was then introduced and the mixture was then treated in the same manner as described in Example 3 whereby 15.1 g (92.9%) of ifenprodil hydrobromide were obtained as white crystals.

The physical characteristics of these catalysts were identical with those of the crystals obtained in Example 2.

EXAMPLE 7

To 4 ml of dioxane were added 6.0 g of 4'-hydroxypropiophenone. 6.4 Grams of bromine were added dropwise to the mixture with stirring at room temperature. The reaction liquid was stirred for an additional 10 minutes and then nitrogen gas was introduced thereinto at a flow rate of 200 ml/minute for 30 minutes at room temperature. To the reaction liquid were then added 7.5 g of 4-benzylpyridine and 100 ml of methanol, and the mixture was refluxed under heating for 5 hours. After replacing the air in the reaction container with nitrogen gas, 3.0 g of 5% palladium-carbon were added and hydrogen was then introduced and the mixture was then treated in the same manner as described in Example 1 whereby 12.5 g (81.1%) of ifenprodil were obtained as white crystals.

The physical characteristics of these crystals were identical with those obtained in Example 1.

EXAMPLE 8

To 4 ml of dioxane were added 6.0 g of 4'-hydroxypropiophenone. 6.4 Grams of bromine were added dropwise to the mixture with stirring at room temperature. The reaction liquid was stirred for an additional 5 minutes and then nitrogen gas was introduced thereinto at a flow rate of 400 ml/minute for 10 minutes at 60° C. To the reaction liquid were then added 6.4 g of 4-benzylpyridine and 50 ml of methanol, and the mixture was refluxed under heating for 5 hours. The reaction mixture was then treated in the same manner as described in Example 3, whereby 11.4 g (70.1%) of ifenprodil hydrobromide were obtained as white crystals.

The physical characteristics of these crystals were identical with those obtained in Example 2.

EXAMPLE 9

To 5 ml of methanol were added 6.0 g of 4'-hydroxypropiophenone. 6.4 Grams of bromine were added dropwise to the mixture with stirring at room temperature. The reaction liquid was stirred for an additional 10 minutes and then nitrogen gas was introduced thereinto at a flow rate of 400 ml/minute for 20 minutes at room temperature. To the reaction liquid were then added 7.5 g of 4-benzylpyridine and 100 ml of methanol, and the mixture was refluxed under heating for 8 hours. The reaction mixture was then treated in the same manner as described in Example 5, whereby 10.2 g (62.7%) of ifenprodil hydrobromide were obtained as white crystals.

The physical characteristics of these crystals were identical with those of the crystals obtained in Example 2.

EXAMPLE 10

To 5 ml of ethanol were added 6.0 g of 4'-hydroxypropiophenone. 6.4 Grams of bromine were added dropwise to the mixture with stirring at room temperature. The reaction liquid was stirred for an additional 10 minutes and then nitrogen gas was introduced thereinto at a flow rate of 100 ml/minute for 30 minutes at 60° C. To the reaction liquid were then added 7.5 g of 4-benzylpyridine and 100 ml of methanol, and the mixture was refluxed under heating for 5 hours. The reaction mixture was then treated in the same manner as described in Example 5, whereby 10.2 g (62.7%) of ifenprodil hydrobromide were obtained as white crystals.

The physical characteristics of these crystals were identical with those of the crystals obtained in Example 2.

EXAMPLE 11

To 5 ml of methanol were added 6.0 g of 4'-hydroxypropiophenone. 6.4 Grams of bromine were added dropwise to the mixture with stirring at room temperature. The reaction liquid was stirred for an additional 10 minutes and then air was introduced thereinto at a flow rate of 200 ml/minute for 30 minutes at room temperature. To the reaction liquid were then added 7.5 g of 4-benzylpyridine and 100 ml of ethanol, and the mixture was refluxed under heating for 5 hours. The reaction mixture was treated in the same manner as described in Example 5, whereby 10.7 g (65.8%) of ifenprodil hydrobromide were obtained as white crystals.

The physical characteristics of these crystals were identical with those of the crystals obtained in Example 2.

EXAMPLE 12

To 4 ml of dioxane were added 6.0 g of 4'-hydroxypropiophenone. 6.4 Grams of bromine were added dropwise to the mixture with stirring at room temperature. The reaction liquid was stirred for an additional 10 minutes and then nitrogen gas was introduced thereinto at a flow rate of 200 ml/minute for 30 minutes at room temperature. To the reaction liquid were then added 7.5 g of 4-benzylpyridine and 100 ml of methanol, and the mixture was refluxed under heating for 5 hours. After replacing the air in the reaction container with nitrogen, 3.0 g of 10% palladium-carbon were added and hydrogen was then introduced and the mixture was stirred for 6 hours at 90°-95° C. under pressure of 50 kg/cm². After completion of the reaction, the catalyst and the like were filtered off and 40 ml of 1-N sodium hydroxide solution were added to the filtrate and the reaction liquid was concentrated under reduced pressure until its whole volume became 30 ml. The residual oily substance was crystallized from a mixture of 10 ml of diethyl ether and 10 ml of petroleum ether under ice cooling and the resultant crude product was recrystallized from isopropanol whereby 12.0 g (77.8%) of ifenprodil were obtained as white crystals.

The physical characteristics of these crystals were identical with those of the crystals obtained in Example 1.

EXAMPLE 13

To a mixture of 3 ml of dioxane and 1 ml of methanol were added 6.0 g of 4'-hydroxypropiophenone. 6.4 Grams of bromine were added dropwise to the mixture with stirring at room temperature. The reaction liquid was stirred for an additional 10 minutes and then nitrogen was introduced thereinto at a flow rate of 400 ml/minute for 15 minutes at 60° C. To the reaction liquid were then added 7.5 g of 4-benzylpyridine and 100 ml of methanol, and the mixture was refluxed under heating for 5 hours. The reaction mixture was then treated in the same manner as described in Example 5, whereby 11.4 g (70.4%) of ifenprodil hydrobromide were obtained as white crystals.

The physical characteristics of these crystals were identical with those of the crystals obtained in Example 2.

EXAMPLE 14

To 10 ml of diethyl ether were added 6.0 g of 4'-hydroxypropiophenone. 6.8 Grams of bromine were added dropwise to the mixture with stirring at room temperature. The reaction mixture was then treated in the same manner as described in Example 5, whereby 13.5 g (83.0%) of ifenprodil hydrobromide were obtained as white crystals.

The physical characteristics of these crystals were identical with those of the crystals obtained in Example 2.

EXAMPLE 15

To 15 ml of di-n-butyl ether were added 6.0 g of 4'-hydroxypropiophenone. 6.8 Grams of bromine were added dropwise to the mixture with stirring at room temperature. The reaction mixture was then treated in the same manner as described in Example 5, whereby 12.8 g (78.7%) of ifenprodil hydrobromide were obtained as white crystals.

The physical characteristics of these crystals were identical with those of the crystals obtained in Example 2.

EXAMPLE 16

To 5 ml of tetrahydrofuran were added 6.0 g of 4'-hydroxypropiophenone. 6.8 Grams of bromine were added dropwise to the mixture with stirring at room temperature. The reaction mixture was then treated in the same manner as described in Example 5, whereby 12.5 g (76.9%) of ifenprodil hydrobromide were obtained as white crystals.

The physical characteristics of these crystals were identical with those of the crystals obtained in Example 2.

EXAMPLE 17

To 4 ml of dioxane were added 6.0 g of 4'-hydroxypropiophenone. 6.4 Grams of bromine were added dropwise to the mixture with stirring at room temperature. The reaction liquid was stirred for an additional 10 minutes and then air was introduced thereinto at a flow rate of 400 ml/minute for 15 minutes at 60° C. To the reaction liquid were then added 7.5 g of 4-benzylpyridine and 50 ml of methanol, and the mixture was refluxed under heating for 5 hours. After replacing the air in the reaction container with nitrogen gas, 2.0 g of 10% palladium-carbon were added and hydrogen was then introduced and the mixture was stirred for 8 hours at 90°-95° C. under pressure of 50 kg/cm². After completion of the reaction, the catalyst and the like were filtered off and 30 ml of 10% ammonia water were added to the filtrate and the reaction liquid was concentrated under reduced pressure until its volume became 20 ml. The residual oily substance was crystallized from a mixture of 15 ml of diethyl ether and 15 ml of petroleum ether under ice cooling and the resultant crude product was recrystallized from isopropanol whereby 10.9 g (70.7%) of ifenprodil were obtained as white crystals.

The physical characteristics of these crystals were identical with those of the crystals obtained in Example 1.

To the mother liquor obtained in the crystallization and recrystallization treatments were added 50 ml of methanol and 40 g of silica gel (Wakogel C-200, Wako Pure Chemicals, Japan). The mixture was concentrated under reduced pressure until dryness. This was layered on 80 g of silica gel (Wakogel C-200) packed into a column (diameter: 2 cm) and eluted with a mixture of 800 ml of chloroform and 200 ml of ethyl acetate. The eluated liquid was discarded. The pack in the column was then eluted with 800 ml of ethyl acetate and the eluate was concentrated under reduced pressure until dryness. The residue was crystallized from isopropanol to obtain 3.9 g (25.3%) of ifenprodil as white crystals.

The physical characteristics of these crystals were identical with those of the crystals obtained in Example 1.

14.8 Grams (96.0%) in toto of ifenprodil were thus obtained.

EXAMPLE 18

To 5 ml of dioxane were added 3.0 g of 4'-hydroxypropiophenone. 3.6 Grams of bromine were added dropwise to the mixture with stirring at room temperature, and the reaction liquid was stirred for an additional 10 minutes. To the reaction liquid were then added 2.0 g of potassium hydrogen carbonate, 3.7 g of 4-benzylpyridine, 40 ml of methanol and 1 ml of water, and the mixture was refluxed under heating for 4 hours. After replacing the air in the reaction container with nitrogen gas, 60 ml of methanol and 1.2 g of 10% palladium-carbon were added and hydrogen was then introduced and the mixture was stirred for 6 hours at 90°-95° C. under pressure of 50 kg/cm². After completion of the reaction, solid matters including the catalyst were filtered off and 60 ml of 3% ammonia water were added to the filtrate and the reaction liquid was concentrated under reduced pressure until its whole volume became about 30 ml. The residual oily substance was crystallized from a mixture of 5 ml of diethyl ether and 5 ml of petroleum ether under ice cooling and the resultant crude product was recrystallized from isopropanol whereby 6.3 g (81.7%) of ifenprodil were obtained as white crystals. M.P. 109°-111° C.

TLC: Rf 0.35

Diatomaceous earth and chloroform-diethylamine (95:5) were used as the support and the developing solvent, respectively. On irradiation of ultra-violet rays and in a color reaction with Dragendorff reagent, a single spot was detected.

NMR absorption spectra (DMSO-d₆; δ ppm):

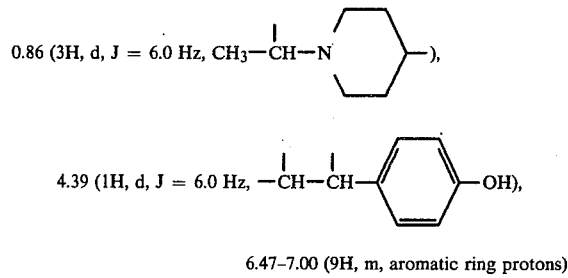

6.47-7.00 (9H, m, aromatic ring protons)

Elementary analysis: as $C_{21}H_{27}NO_2 \cdot C_3H_8O$: Calc.: C, 74.76%; H, 9.15%, N, 3.63% Found: C, 74.68%; H, 9.17%; N, 3.79%

EXAMPLE 19

To 5 ml of dioxane were added 3.0 g of 4'-hydroxypropiophenone. 3.6 Grams of bromine were added dropwise to the mixture with stirring at room temperature, and the reaction liquid was stirred for an additional 10 minutes. To the reaction liquid were then added 7.4 g of 4-benzylpyridine and 40 ml of methanol, and the mixture was refluxed under heating for 5 hours. After replacing the air in the reaction container with nitrogen gas, 60 ml of methanol and 2.0 g of 10% palladium-carbon were added and hydrogen was then introduced and the mixture was stirred for 8 hours at 90°-95° C. under pressure of 50 kg/cm². After completion of the reaction, solid matters including the catalyst were filtered off and the filtrate was concentrated under reduced pressure and the residual oily substance was washed with water. 10 Milliliters of diethyl ether were added to the oily substance under ice cooling and the precipitated crystals were collected and recrystallized from ethanol whereby 7.6 g (93.5%) of ifenprodil hydrobromide were obtained as white crystals. M.P. 188°-191° C.

TLC: Rf 0.35

Diatomaceous earth and chloroform-diethylamine (95:5) were used as the support and the developing solvent, respectively. On irradiation of ultra-violet rays and in a color reaction with Dragendorff reagent, a single spot was detected.

NMR absorption spectra (DMSO-d₆; δ ppm):

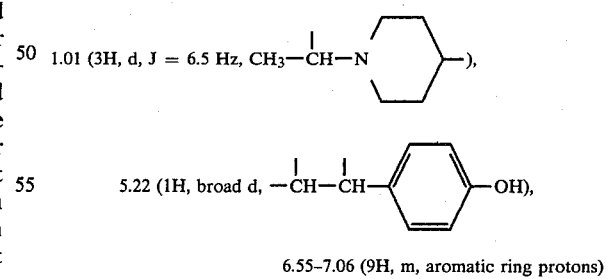

6.55-7.06 (9H, m, aromatic ring protons)

Elementary analysis: as $C_{21}H_{27}NO_2 \cdot HBr$ Calc: C, 62.07%; H, 6.94%; N, 3.45% Found: C, 62.17%, H, 7.00%; N, 3.25%

EXAMPLE 20

To 4 ml of dioxane were added 6.0 g of 4'-hydroxypropiophenone. 6.4 Grams of bromine were added dropwise to the mixture with stirring at room temperature, and the reaction liquid was stirred for an additional 5 minutes. To the reaction liquid were then added 14.8 g of 4-benzylpyridine and 100 ml of methanol, and the mixture was refluxed under heating for 3 hours. After replacing the air in the reaction container with nitrogen gas, 3.0 g of 5% palladium-carbon were added and hydrogen was then introduced and the mixture was stirred for 8 hours at 90°–95° C. under pressure of 50 kg/cm$^2$. After completion of the reaction, solid matters including the catalyst were filtered off and 30 ml of 10% ammonia water were added to the filtrate and the reaction liquid was concentrated under reduced pressure until its whole volume became about 30 ml. The residue was crystallized from diethyl ether and recrystallized from isopropanol whereby 11.4 g (74.0%) of ifenprodil were obtained as white crystals.

The physical characteristics of these crystals were identical with those of the crystals obtained in Example 18.

EXAMPLE 21

To 10 ml of diethyl ether were added 3.0 g of 4'-hydroxypropiophenone. 3.6 Grams of bromine were added dropwise to the mixture with stirring at room temperature. The reaction mixture was then treated in the same manner as described in Example 18, whereby 4.8 g (62.3%) of ifenprodil were obtained as white crystals.

The physical characteristics of these crystals were identical with those of the crystals obtained in Example 18.

EXAMPLE 22

To 5 ml of dioxane were added 3.0 g of 4'-hydroxypropiophenone. 3.6 Grams of bromine were added dropwise to the mixture with stirring at room temperature, and the reaction liquid was stirred for an additional 10 minutes. To the reaction liquid were then added 1.7 g of anhydrous sodium acetate, 3.7 g of 4-benzylpyridine and 40 ml of methanol, and the mixture was refluxed under heating for 5 hours. After replacing the air in the reaction container with nitrogen gas, 60 ml of methanol and 3.0 g of 10% palladium-carbon were added and hydrogen was then introduced and the mixture was stirred for 8 hours at 90°–95° C. under pressure of 20 kg/cm$^2$. The reaction mixture was then treated in the same manner as described in Example 18, whereby 4.7 g (61.0%) of ifenprodil were obtained as white crystals.

The physical characteristics of these crystals were identical with those of the crystals obtained in Example 18.

EXAMPLE 23

To 5 ml of methanol were added 3.0 g of 4'-hydroxypropiophenone. 3.6 Grams of bromine were added dropwise to the mixture with stirring at room temperature. The reaction liquid was then treated in the same manner as described in Example 18, whereby 4.3 g (55.8%) of ifenprodil were obtained as white crystals.

The physical characteristics of these crystals were identical with those of the crystals obtained in Example 18.

EXAMPLE 24

To 5 ml of di-n-butyl ether were added 3.0 g of 4'-hydroxypropiophenone. 3.6 Grams of bromine were added dropwise to the mixture with stirring at room temperature. The reaction liquid was then treated in the same manner as described in Example 18, whereby 4.4 g (57.1%) of ifenprodil were obtained as white crystals.

The physical characteristics of these crystals were identical with those of the crystals obtained in Example 18.

EXAMPLE 25

To 5 ml of tetrahydrofuran were added 3.0 g of 4'-hydroxypropiophenone. 3.6 Grams of bromine were added dropwise to the mixture with stirring at room temperature. The reaction liquid was then treated in the same manner as described in Example 18, whereby 4.6 g (59.7%) of ifenprodil were obtained as white crystals.

The physical characteristics of these crystals were identical with those of the crystals obtained in Example 18.

EXAMPLE 26

To 4 ml of dioxane were added 6.0 g of 4'-hydroxypropiophenone. 6.4 Grams of bromine were added dropwise to the mixture with stirring at room temperature, and the reaction liquid was stirred for an additional 10 minutes. To the reaction liquid were then added 7.5 g of 4-benzylpyridine, 1 ml of water, 100 ml of ethanol and 4.0 g of potassium hydrogen carbonate, and the mixture was refluxed under heating for 5 hours. After replacing the air in the reaction container with nitrogen gas, 2.0 g of 10% palladium-carbon were added and hydrogen was then introduced and the mixture was stirred for 8 hours at 90°–95° C. under pressure of 50 kg/cm$^2$. After completion of the reaction, solid matters including the catalyst were filtered off and the filtrate was concentrated under reduced pressure until dryness. The residue was washed with ice water and then crystallized from acetone and the resultant crude product was recrystallized from ethanol whereby 13.7 g (84.3%) of ifenprodil hydrobromide were obtained as white crystals.

The physical characteristics of these crystals were identical with those of the crystals obtained in Example 19.

EXAMPLE 27

To 10 ml of ethanol were added 6.0 g of 4'-hydroxypropiophenone. 6.4 Grams of bromine were added dropwise to the mixture with stirring at room temperature and the reaction liquid was stirred for an additional 10 minutes. To the reaction liquid were then added 7.5 g of 4-benzylpyridine, 100 ml of ethanol and 3.28 g of anhydrous sodium acetate, and the mixture was refluxed under heating for 5 hours. After replacing the air in the reaction container with nitrogen gas, 2.0 g of 10% palladium-carbon were added and hydrogen was then introduced and the mixture was then treated in the same manner as described in Example 20, whereby 8.5 g (55.1%) of ifenprodil were obtained as white crystals.

The physical characteristics of these crystals were identical with those of the crystals obtained in Example 18.

EXAMPLE 28

To 4 ml of dioxane were added 6.0 g of 4'-hydroxypropiophenone. 6.4 Grams of bromine were added dropwise to the mixture with stirring at room temperature, and the reaction liquid was stirred for an additional 5 minutes. To the reaction liquid were then added 7.5 g of 4-benzylpyridine, 100 ml of methanol and 2.0 g of potassium carbonate, and the mixture was refluxed under heating for 5 hours. The reaction mixture was then treated in the same manner as described in Example 26, whereby 12.2 g (75.0%) of ifenprodil hydrobromide were obtained as white crystals.

The physical characteristics of these crystals were identical with those of the crystals obtained in Example 19.

EXAMPLE 29

To 4 ml of dioxane were added 6.0 g of 4'-hydroxypropiophenone. 6.4 Grams of bromine were added dropwise to the mixture with stirring at room temperature, and the reaction liquid was stirred for an additional 10 minutes. To the reaction liquid were then added 7.5 g of 4-benzylpyridine, 100 ml of methanol, and 2.8 ml of 10 N potassium hydroxide solution, and the mixture was refluxed under heating for 5 hours. After replacing the air in the reaction container with nitrogen gas, 3.0 g of 10% palladium-carbon were added and hydrogen was then introduced and the mixture was stirred for 8 hours at 60°–70° C. under pressure of 50 kg/cm$^2$. The reaction mixture was then treated in the same manner as described in Example 26, whereby 12.1 g (74.4%) of ifenprodil hydrobromide were obtained as white crystals.

The physical characteristics of these crystals were identical with those of the crystals obtained in Example 19.

EXAMPLE 30

To 4 ml of dioxane were added 6.0 g of 4'-hydroxypropiophenone. 6.4 Grams of bromine were added dropwise to the mixture with stirring at room temperature, and the reaction liquid was stirred for an additional 10 minutes. To the reaction liquid were then added 7.5 g of 4-benzylpyridine, 100 ml of methanol and 2.8 ml of 10 N sodium hydroxide solution, and the mixture was refluxed under heating for 5 hours. After replacing the air in the reaction container with nitrogen gas, 2.0 g of 10% palladium-carbon were added and hydrogen was then introduced and the mixture was stirred for 8 hours at 90°–95° C. under pressure of 50 kg/cm$^2$. After completion of the reaction, solid matters including the catalyst were filtered off and 40 ml of 1 N sodium hydroxide solution were added to the filtrate and the reaction liquid was concentrated under reduced pressure until its whole volume became 30 ml. The residual oily substance was crystallized from a mixture of 10 ml of diethyl ether and 10 ml of petroleum ether under ice cooling and the resultant crude product was recrystallized from isopropanol whereby 12.0 g (77.8%) of ifenprodil were obtained as white crystals.

The physical characteristics of these crystals were identical with those of the crystals obtained in Example 18.

EXAMPLE 31

To 4 ml of dioxane were added 6.0 g of 4'-hydroxypropiophenone. 6.4 Grams of bromine were added dropwise to the mixture with stirring at room temperature, and the reaction liquid was stirred for an additional 10 minutes. To the reaction liquid were then added 6.4 g of 4-benzylpyridine, 1 ml of water, 100 ml of methanol and 4.0 g of potassium hydrogen carbonate, and the mixture was refluxed under heating for 5 hours. The reaction mixture was then treated in the same manner as described in Example 26, whereby 10.6 g (66.4%) of ifenprodil hydrobromide were obtained as white crystals.

The physical characteristics of these crystals were identical with those of the crystals obtained in Example 19.

EXAMPLE 32

To a mixture of 3 ml of dioxane and 1 ml of methanol were added 6.0 g of 4'-hydroxypropiophenone. 6.4 Grams of bromine were added dropwise to the mixture with stirring at room temperature, and the reaction liquid was stirred for an additional 10 minutes. To the reaction liquid were then added 7.5 g of 4-benzylpyridine, 100 ml of ethanol and 3.28 g of anhydrous sodium acetate, and the mixture was refluxed under heating for 5 hours. The reaction mixture was then treated in the same manner as described in Example 27, whereby 11.2 g (72.6%) of ifenprodil were obtained as white crystals.

The physical characteristics of these crystals were identical with those of the crystals obtained in Example 18.

EXAMPLE 33

To 5 ml of dioxane were added 3.0 g of 4'-hydroxypropiophenone. 3.6 Grams of bromine were added dropwise to the mixture with stirring at room temperature, and the reaction liquid was stirred for an additional 10 minutes. To the reaction liquid were then added 2.0 g of potassium hydrogen carbonate, 3.7 g of 4-benzylpyridine, 40 ml of methanol, and 1 ml of water, and the mixture was refluxed under heating for 4 hours. After replacing the air in the reaction container with nitrogen gas, 60 ml of methanol and 1.2 g of 10% palladium-carbon were added and hydrogen was then introduced and the mixture was stirred for 6 hours at 90°–95° C. under pressure of 50 kg/cm$^2$. After completion of the reaction, solid matters including the catalyst were filtered off and 60 ml of 3% ammonia water were added to the filtrate and the reaction liquid was concentrated under reduced pressure until its whole volume became about 30 ml. The residual oily substances was crystallized from a mixture of 5 ml of diethyl ether and 5 ml of petroleum ether under ice cooling and the precipitated crude crystals were recrystallized from isopropanol whereby 6.2 g (80.4%) of ifenprodil were obtained as white crystals.

The physical characteristics of these crystals were identical with those of the crystals obtained in Example 18.

To the filtrate, i.e. mother liquid, obtained in the above crystallization and recrystallization treatments were added 50 ml of methanol and 20 g of silica gel (Wakogel C-200). The mixture was heated under reduced pressure until dryness and layered on 60 g of silica gel (Wakogel C-200) charged into a column (diameter: 2 cm). The pack in the column was eluated with a mixture of 400 ml of chloroform and 100 ml of ethyl acetate and the eluate was discarded. The pack was then eluated with 500 ml of ethyl acetate and the eluate was concentrated under reduced pressure until dryness. The residue was recrystallized from isopropanol whereby 1.0 g (13.0%) of ifenprodil was obtained as white crystals. The physical characteristics of these crystals were identical with those of the crystals obtained in Example 18. 7.2 Grams (93.4%) in toto of ifenprodil were thus obtained.

EXAMPLE 34

To 4 ml of dioxane were added 6.0 g of 4'-hydroxypropiophenone. 6.8 Grams of bromine were added dropwise to the mixture with stirring at room temperature. The reaction liquid was stirred for an additional 10 minutes and then nitrogen was introduced thereinto at a flow rate of 200 ml/minute for 1 hour at 60° C. To the reaction liquid were then added 7.5 g of 4-benzylpyridine and 100 ml of methanol, and the mixture was refluxed under heating for 5 hours. After stopping the heating, 0.3 g of platinum oxide were added and hydrogen was then introduced and the mixture was stirred for 9 hours under pressure of about 1 atm. After completion of the reaction, solid matters including the catalyst were filtered off and the filtrate was concentrated under reduced pressure until dryness. The residue was washed with 15 ml of diethyl ether and recrystallized from ethanol whereby 11.5 g (71.0%) of ifenprodil hydrobromide were obtained as white crystals. M.P. 188°–191° C.

TLC: Rf 0.35

[Diatomaceous earth and chloroform-diethylamine (95:5) were used as the support and the developing solvent, respectively. On irradiation of ultra-violet rays and in a color reaction with Dragendorff reagent, a single spot was detected.]

NMR absorption spectra (DMSO-$d_6$; δ ppm):

1.01 (3H, d, J = 6.5 Hz, $CH_3-CH-N$⟨ ⟩), 5.22 (1H, broad d, $-CH-CH-$⟨ ⟩$-OH$), 6.55–7.06 (9H, m, aromatic ring protons)

Elementary analysis: as $C_{21}H_{27}NO_2 \cdot HBr$: Calc.: C, 62.07%; H, 6.94%; N, 3.45%. Found: C, 61.86%; H, 7.13%; N, 3.34%.

EXAMPLE 35

To 4 ml of dioxane were added 6.0 g of 4'-hydroxypropiophenone. 6.8 Grams of bromine were added dropwise to the mixture with stirring at room temperature. The reaction liquid was stirred for an additional 10 minutes and then nitrogen was introduced thereinto at a flow rate of 400 ml/minute for 10 minutes at 60° C. To the reaction liquid were then added 8.1 g of 4-benzylpyridine and 100 ml of methanol, and the mixture was refluxed under heating for 5 hours. After stopping the heating, 0.3 g of platinum oxide were added and hydrogen was then introduced, and the mixture was stirred for 8 hours under pressure of about 1 atm. After completion of the reaction, solid matters including the catalyst were filtered off and 30 ml of 10% ammonia water were added to the filtrate and the reaction liquid was concentrated under reduced pressure until dryness. The residue was taken up in 100 ml of methanol and 100 g of silica gel (Wakogel C-200) were added thereto. The mixture was heated under reduced pressure until dryness and layered on 150 g of silica gel (Wakogel C-200) charged into a column (diameter: 4 cm). The pack in the column was eluated with a mixture of 2 l of chloroform and 500 ml of ethyl acetate and the eluate was discarded. The pack was then eluated with 1.5 l of ethyl acetate and the eluate was concentrated under reduced pressure until dryness. The residue was crystallized from isopropanol whereby 12.5 g (81.2%) of ifenprodil were obtained as white crystals. M.P. 109°–111° C.

TLC: Rf 0.35

[Diatomaceous earth and chloroform-diethylamine (95:5) were used as the support and the developing solvent, respectively. On irradiation of ultra-violet rays and in a color reaction with Dragendorff reagent, a single spot was detected.]

NMR absorption spectra (DMSO-$d_6$; δ ppm):

0.86 (3H, d, J = 6.0 Hz, $CH_3-CH-N$⟨ ⟩), 4.39 (1H, d, J = 6.0 Hz, $-CH-CH-$⟨ ⟩$-OH$), 6.47–7.00 (9H, m, aromatic ring protons)

Elementary analysis: as $C_{21}H_{27}NO_2 \cdot C_3H_8O$: Calc.: C, 74.76%; H, 9.15%; N, 3.63%. Found: C, 74.69%; H, 9.19%; N, 3.70%.

EXAMPLE 36

To 4 ml of dioxane were added 6.0 g of 4'-hydroxypropiophenone. 6.8 Grams of bromine were added dropwise to the mixture with stirring at room temperature. The reaction liquid was stirred for an additional 5 minutes and then nitrogen was introduced thereinto at a flow rate of 400 ml/minute for one hour at room temperature. To the reaction liquid were than added 6.8 g of 4-benzylpyridine and 50 ml of methanol, and the mixture was refluxed under heating for 4 hours. After stopping the heating, 0.2 g of platinum oxide and 50 ml of methanol were added and hydrogen gas was then introduced and the mixture was stirred for 9 hours under pressure of about 1 atm. After completion of the reaction, the reaction mixture was treated in the same manner as described in Example 34, whereby 10.0 g (61.7%) of ifenprodil hydrobromide were obtained as white crystals.

The physical characteristics of these crystals were identical with those of the crystals obtained in Example 34.

EXAMPLE 37

To 4 ml of dioxane were added 6.0 g of 4'-hydroxypropiophenone. 6.8 Grams of bromine were added dropwise to the mixture with stirring at room temperature. The reaction liquid was stirred for an additional 5 minutes and then air was introduced thereinto at a flow rate of 200 ml/minute for one hour at room temperature. To the reaction liquid were then added 7.5 g of 4-benzylpyridine and 50 ml of methanol, and the mixture was refluxed under heating for 4 hours. After stopping the heating, 0.5 g of platinum oxide and 50 ml of methanol were added and hydrogen was then introduced and the mixture was stirred for 7 hours under pressure of about 1 atm. After completion of the reaction, the catalyst was filtered off and 30 ml of 10% ammonia water were added to the filtrate and the reaction liquid was concentrated under reduced pressure until dryness. The residue was crystallized from a mixture of 15 ml of diethyl ether and 15 ml of petroleum ether under ice cooling and the resultant crude product was recrystallized from isopropanol whereby 10.2 g (66.2%) of ifenprodil were obtained as white crystals.

The physical characteristics of these crystals were identical with those of the crystals obtained in Example 35.

EXAMPLE 38

To 4 ml of dioxane were added 6.0 g of 4'-hydroxypropiophenone. 6.8 Grams of bromine were added dropwise to the mixture with stirring at room temperature. The reaction liquid was stirred for an additional 5 minutes and then air was introduced thereinto at a flow rate of 100 ml/minute for one hour at 60° C. To the reaction liquid were then added 8.1 g of 4-benzylpyridine and 100 ml of ethanol, and the mixture was refluxed under heating for 5 hours. After stopping the heating, 0.3 g of platinum oxide and 200 ml of ethanol were added and hydrogen was then introduced and the mixture was stirred for 12 hours under pressure of about 1 atm. After completion of the reaction, the reaction mixture was treated in the same manner as described in Example 34, whereby 10.7 g (66.0%) of ifenprodil hydrobromide were obtained as white crystals.

The physical characteristics of these crystals were identical with those of the crystals obtained in Example 34.

EXAMPLE 39

To 15 ml of di-n-butyl ether were added 6.0 g of 4'-hydroxypropiophenone. 6.6 Grams of bromine were added dropwise to the mixture with stirring at room temperature. The reaction liquid was stirred for an additional 10 minutes and then nitrogen was introduced thereinto at a flow rate of 200 ml/minute for one hour at room temperature. To the treaction liquid were then added 7.5 g of 4-benzylpyridine and 100 ml of methanol, and the mixture was refluxed under heating for 5 hours. After stopping the heating, the reaction mixture was treated in the same manner as described in Example 35, whereby 11.3 g (73.4%) of ifenprodil were obtained as white crystals.

The physical characteristics of these crystals were identical with those of the crystals obtained in Example 35.

EXAMPLE 40

To 15 ml of diethyl ether were added 6.0 g of 4'-hydroxypropiophenone. 6.6 Grams of bromine were added dropwise to the mixture with stirring at room temperature. After the addition of bromine, the reaction mixture was treated in the same manner as described in Example 39, whereby 12.0 g (77.9%) of ifenprodil were obtained as white crystals.

The physical characteristics of these crystals were identical with those of the crystals obtained in Example 35.

EXAMPLE 41

To 5 ml of tetrahydrofuran were added 6.0 g of 4'-hydroxypropiophenone. 6.8 Grams of bromine were added dropwise to the mixture with stirring at room temperature. After the addition of bromine, the reaction mixture was treated in the same manner as described in Example 35, whereby 11.5 g (74.7%) of ifenprodil were obtained as white crystals.

The physical characteristics of these crystals were identical with those of the crystals obtained in Example 35.

EXAMPLE 42

To 10 ml of methanol were added 6.0 g of 4'-hydroxypropiophenone. 6.4 Grams of bromine were added dropwise to the mixture with stirring at room temperature. After the addition of bromine, the reaction mixture was treated in the same manner as described in Example 35, whereby 9.0 g (58.4%) of ifenprodil were obtained as white crystals.

The physical characteristics of these crystals were identical with those of the crystals obtained in Example 35.

EXAMPLE 43

To 7 ml of ethanol were added 6.0 g of 4'-hydroxypropiophenone. 6.6 Grams of bromine were added dropwise to the mixture with stirring at room temperature. After the addition of bromine, the reaction mixture was treated in the same manner as described in Example 35, whereby 8.8 g (57.1%) of ifenprodil were obtained as white crystals.

The physical characteristics of these crystals were identical with those of the crystals obtained in Example 35.

EXAMPLE 44

To a mixture of 5 ml of dioxane and 1 ml of methanol were added 6.0 g of 4'-hydroxypropiophenone. 6.6 Grams of bromine were added dropwise to the mixture with stirring at room temperature. After the addition of bromine, the reaction mixture was treated in the same manner as described in Example 35, whereby 10.1 g (65.6%) of ifenprodil were obtained as white crystals.

The physical characteristics of these crystals were identical with those of the crystals obtained in Example 35.

EXAMPLE 45

To 4 ml of dioxane were added 6.0 g of 4'-hydroxypropiophenone. 6.8 Grams of bromine were added dropwise to the mixture with stirring at room temperature, and the reaction liquid was stirred for an additional 10 minutes. To the reaction liquid were then added 7.5 g of 4-benzylpyridine, 1 ml of water, 4.0 g of potassium hydrogen carbonate and 50 ml of methanol, and the mixture was refluxed under heating for 5 hours. After stopping the heating, 50 ml of methanol and 0.2 g of platinum oxide were added and hydrogen was then introduced and the mixture was stirred for 8 hours under pressure of about 1 atm. After completion of the reaction, solid matters including the catalyst were filtered off and the filtrate was concentrated under reduced pressure until dryness. The residue was washed with 10 ml of ice water and then with 15 ml of diethyl ether and the resultant crude product was recrystallized from ethanol whereby 11.1 g (68.5%) of ifenprodil hydrobromide were obtained as white crystals. M.P. 188°–191° C.

TLC: Rf 0.35

Diatomaceous earth and chloroform-diethylamine (95:5) were used as the support and the developing solvent, respectively. On irradiation of ultra-violet rays and in a color reaction with Dragendorff reagent, a single spot was detected.

NMR absorption spectra (DMSO-$d_6$; δ ppm):

1.01 (3H, d, J = 6.5 Hz, CH$_3$—CH—N⟨ ⟩—), 5.22 (1H, broad d, —CH—CH—⟨ ⟩—OH), 6.55–7.06 (9H, m, aromatic ring protons)

Elementary analysis: as C$_{21}$H$_{27}$NO$_2$·HBr: Calc.: C, 62.07%; H, 6.94%; N, 3.45%. Found: C, 62.00%; H, 7.11%; N, 3.22%.

EXAMPLE 46

To 4 ml of dioxane were added 6.0 g of 4′-hydroxypropiophenone. 6.8 Grams of bromine were added dropwise to the mixture with stirring at room temperature, and the reaction liquid was stirred for an additional 10 minutes. To the reaction liquid were then added 6.8 g of 4-benzylpyridine, 4.0 g of potassium hydrogen carbonate, 50 ml of methanol and 1 ml of water, and the mixture was refluxed under heating for 5 hours. After stopping the heating, 50 ml of methanol and 0.2 g of platinum oxide were added and hydrogen was then introduced and the mixture was stirred for 8 hours under pressure of about 1 atm. After completion of the reaction, solid matters including the catalyst were filtered off and 30 ml of 10% ammonia water were added to the filtrate and the reaction liquid was concentrated under reduced pressure until dryness. The residue was washed with 10 ml of ice water and then dissolved in 100 ml of methanol. 100 Grams of silica gel (Wakogel C-200) were added to the solution and the mixture was heated under reduced pressure until dryness. The residue was layered on 100 g of silica gel (Wakogel C-200) charged into a column (diameter: 4 cm). The pack in the column was eluated with a mixture of 2 l of chloroform and 500 ml of ethyl acetate and the eluate was discarded. The pack was then eluated with 1.5 l of ethyl acetate and the eluate was concentrated under reduced pressure until dryness. The residue was recrystallized from isopropanol whereby 12.3 g (79.9%) of ifenprodil were obtained as white crystals. M.P. 109°–111° C.

TLC: Rf 0.35

Diatomaceous earth and chloroform-diethylamine (95:5) were used as the support and the developing solvent, respectively. On irradiation of ultra-violet rays and in a color reaction with Dragendorff reagent, a single spot was detected.

NMR absorption spectra (DMSO-d$_6$; δ ppm):

0.86 (3H, d, J = 6.0 Hz, CH$_3$—CH—N⟨ ⟩—), 4.39 (1H, d, J = 6.0 Hz, —CH—CH—⟨ ⟩—OH), 6.47–7.00 (9H, m, aromatic ring protons)

Elementary analysis: as C$_{21}$H$_{27}$NO$_2$·C$_3$H$_8$O: Calc.: C, 74.76%; H, 9.15%; N, 3.63%. Found: C, 74.65%; H, 9.05%; N, 3.80%.

EXAMPLE 47

To 4 ml of dioxane were added 6.0 g of 4′-hydroxypropiophenone. 6.8 Grams of bromine were added dropwise to the mixture with stirring at room temperature, and the reaction liquid was stirred for an additional 10 minutes. To the reaction liquid were then added 7.5 g of 4-benzylpyridine, 2.1 g of potassium carbonate, 1 ml of water and 50 ml of methanol, and the mixture was refluxed under heating for 5 hours. After stopping the heating, 25 ml of methanol and 0.2 g of platinum oxide were added and hydrogen was then introduced and the mixture was stirred for 8 hours under pressure of about 1 atm. After completion of the reaction, the reaction mixture was worked up in the same manner as described in Example 46, whereby 12.0 g (77.9%) of ifenprodil were obtained as white crystals.

The physical characteristics of these crystals were identical with those of the crystals obtained in Example 46.

EXAMPLE 48

To 4 ml of dioxane were added 6.0 g of 4′-hydroxypropiophenone. 6.8 Grams of bromine were added dropwise to the mixture with stirring at room temperature, and the reaction liquid was stirred for an additional 5 minutes. To the reaction liquid were then added 7.5 g of 4-benzylpyridine, 2.8 ml of 10-N sodium hydroxide solution and 100 ml of methanol, and the mixture was refluxed under heating for 5 hours. After stopping the heating, 0.5 g of platinum oxide were added and hydrogen was then introduced and the mixture was stirred for 7 hours under pressure of about 1 atm. After completion of the reaction, the reaction mixture was worked up in the same manner as described in Example 46, whereby 11.5 g (74.7%) of ifenprodil were obtained as white crystals.

The physical characteristics of these crystals were identical with those of the crystals obtained in Example 46.

EXAMPLE 49

To 4 ml of dioxane were added 6.0 g of 4′-hydroxypropiophenone. 6.8 Grams of bromine were added dropwise to the mixture with stirring at room temperature, and the reaction liquid was stirred for an additional 5 minutes. To the reaction liquid were than added 7.5 g of 4-benzylpyridine, 2.8 ml of 10-N sodium hydroxide and 100 ml of methanol, and the mixture was refluxed under heating for 5 hours. After stopping and heating, 0.5 g of platinum oxide were added and hydrogen was then introduced and the mixture was stirred for 7 hours under pressure of about 1 atm. After completion of the reaction, solid matters including the catalyst were filtered off and 30 ml of 10% ammonia water were added to the filtrate and the reaction liquid was concentrated under reduced pressure until its volume became 20 ml. The residual oily substance was crystallized from a mixture of 15 ml of diethyl ether and 15 ml of petroleum ether under ice cooling and the resultant crude product was recrystallized from isopropanol whereby 8.9 g (57.8%) of ifenprodil were obtained as white crystals.

The physical characteristics of these crystals were identical with those of the crystals obtained in Example 46.

EXAMPLE 50

To 4 ml of dioxane were added 6.0 g of 4'-hydroxypropiophenone. 6.8 Grams of bromine were added dropwise to the mixture with stirring at room temperature, and the reaction liquid was stirred for an additional 5 minutes. To the reaction liquid were then added 8.1 g of 4-benzylpyridine, 100 ml of methanol and 3.3 g of anhydrous sodium acetate, and the mixture was refluxed under heating for 5 hours. After refluxing the mixture, the reaction mixture was worked up in the same manner as described in Example 46, whereby 12.3 g (79.9%) of ifenprodil were obtained as white crystals.

The physical characteristics of these crystals were identical with those of the crystals obtained in Example 46.

EXAMPLE 51

To 4 ml of dioxane were added 6.0 g of 4'-hydroxypropiophenone. 6.8 Grams of bromine were added dropwise to the mixture with stirring at room temperature, and the reaction liquid was stirred for an additional 10 minutes. To the reaction liquid were then added 7.5 g of 4-benzylpyridine, 3.3 g of anhydrous sodium acetate and 100 ml of ethanol, and the mixture was refluxed under heating for 3 hours. After stopping the heating, 0.5 g of platinum oxide and 200 ml of ethanol were added and hydrogen was then introduced and the mixture was stirred for 9 hours under pressure of about 1 atm. After completion of the reaction, the reaction mixture was treated in the same manner as described in Example 46, whereby 10.9 g (70.8%) of ifenprodil were obtained as white crystals.

The physical characteristics of these crystals were identical with those of the crystals obtained in Example 46.

EXAMPLE 52

To 4 ml of dioxane were added 6.0 g of 4'-hydroxypropiophenone. 6.8 Grams of bromine were added dropwise to the mixture with stirring at room temperature, and the reaction liquid was stirred for an additional 10 minutes. To the reaction liquid were then added 14.3 g of 4-benzylpyridine and 100 ml of methanol, and the mixture was refluxed under heating for 3 hours. After stopping the heating, 0.5 g of platinum oxide were added and hydrogen was then introduced and the mixture was stirred for 12 hours under pressure of about 1 atm. After completion of the reaction, the reaction mixture was worked up in the same manner as described in Example 45, whereby 12.0 g (74.1%) of ifenprodil hydrobromide were obtained as white crystals.

The physical characteristics of these crystals were identical with those of the crystals obtained in Example 45.

EXAMPLE 53

To 10 ml of di-n-butyl ether were added 6.0 g of 4'-hydroxypropiophenone. 6.6 Grams of bromine were added dropwise to the mixture with stirring at room temperature, and the reaction liquid was stirred for an additional 10 minutes. To the reaction liquid were then added 7.5 g of 4-benzylpyridine, 4.0 g of potassium hydrogen carbonate, 1 ml of water and 50 ml of methanol, and the mixture was refluxed under heating for 5 hours. After stopping the heating, the reaction mixture was treated in the same manner as described in Example 46, whereby 11.7 g (76.0%) of ifenprodil were obtained as white crystals.

The physical characteristics of these crystals were identical with those of the crystals obtained in Example 46.

EXAMPLE 54

To 15 ml of diethyl ether were added 6.0 g of 4'-hydroxypropiophenone. 6.4 Grams of bromine were added dropwise to the mixture with stirring at room temperature. After the addition of bromine, the reaction mixture was treated in the same manner as described in Example 53, whereby 11.7 g (76.0%) of ifenprodil were obtained as white crystals.

The physical characteristics of these crystals were identical with those of the crystals obtained in Example 46.

EXAMPLE 55

To 5 ml of tetrahydrofuran were added 6.0 g of 4'-hydroxypropiophenone. 6.8 Grams of bromine were added dropwise to the mixture with stirring at room temperature. After the addition of bromine, the reaction mixture was treated in the same manner as described in Example 46, whereby 11.5 g (74.7%) of ifenprodil were obtained as white crystals.

The physical characteristics of these crystals were identical with those of the crystals obtained in Example 46.

EXAMPLE 56

To 10 ml of methanol were added 6.0 g of 4'-hydroxypropiophenone. 6.4 Grams of bromine were added dropwise to the mixture with stirring at room temperature. After the addition of bromine, the reaction mixture was treated in the same manner as described in Example 53, whereby 8.8 g (57.1%) of ifenprodil were obtained as white crystals.

The physical characteristics of these crystals were identical with those of the crystals obtained in Example 46.

EXAMPLE 57

To 7 ml of ethanol were added 6.0 g of 4'-hydroxypropiophenone. 6.6 Grams of bromine were added dropwise to the mixture with stirring at room temperature. After the addition of bromine, the reaction mixture was treated in the same manner as described in Example 51, whereby 8.5 g (55.2%) of ifenprodil were obtained as white crystals.

The physical characteristics of these crystals were identical with those of the crystals obtained in Example 46.

EXAMPLE 58

To 5 ml of dioxane were added 6.0 g of 4'-hydroxypropiophenone. 6.0 Grams of bromine were added dropwise to the mixture with stirring at room temperature. After the addition of bromine, the reaction mixture was treated in the same manner as described in Example 53, whereby 10.3 g (66.9%) of ifenprodil were obtained as white crystals.

The physical characteristics of these crystals were identical with those of the crystals obtained in Example 46.

EXAMPLE 59

4.8 Grams of ifenprodil hydrobromide were dissolved in 25 ml of hot methanol and 100 ml of 3% ammonia water were added thereto. The mixture was stirred and concentrated under reduced pressure until its whole volume became about 30 ml. The residue was crystallized from 15 ml of isopropanol whereby 4.3 g (94.5%) of ifenprodil were obtained as white crystals.

The physical characteristics of these crystals were identical with those of the crystals obtained in Example 46.

EXAMPLE 60

5.0 Grams of ifenprodil were added to a solution of 1.0 g of tartaric acid in 15 ml of methanol, and the mixture was stirred until the ifenprodil was dissolved. The solution was cooled and the precipitated crystals were collected by filtration. The product was washed with methanol and then dried whereby 5.0 g (92.8%) of ifenprodil tartrate were obtained as white crystals.

M.P.: 140°–148° C.

TLC: Rf 0.35

[Diatomaceous earth and chloroform-diethylamine (95:5) were used as the support and the developing solvent, respectively. On irradiation of ultra-violet rays and is a color reaction with Dragendorff reagent, a single spot was detected.]

NMR absorption spectra (DMSO-d$_6$; δ ppm):

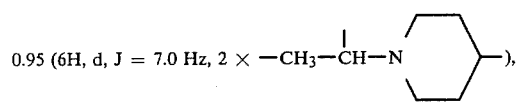

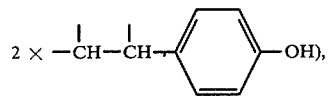

6.55–7.04 (18H, m, aromatic ring protons)

Elementary analysis: as $(C_{21}H_{27}NO_2)_2 \cdot C_4H_6O_6 \cdot 12/7\text{-}H_2O$: Calc.: C, 66.42%; H, 7.69%; N, 3.37%. Found: C, 66.55%; H, 7.80%; N, 3.48%.

It is understood that the preceding representative examples may be varied within the scope of the present specification both as to reactants and reaction conditions, by one skilled in the art to achieve essentially the same results.

As many widely different embodiments of this invention may be made without departing from the spirit and scope thereof, it is to be construed that this invention is not limited to the specific embodiments thereof except as defined in the appended claims.

What is claimed is:

1. A process for the preparation of 1-(4-hydroxyphenyl)-2-(4-benzylpiperidino)-1-propanol and acid-addition salts thereof in a single reaction container, which comprises brominating 4'-hydroxypropriophenone in a single or mixed solvent selected from the group consisting of methanol, ethanol and a saturated aliphatic ether, removing hydrogen bromide formed in the course of the bromination, adding 4-benzylpyridine and a single or mixed solvent selected from the group consisting of methanol and ethanol to the reaction mixture, heating the reaction mixture under reflux and then subjecting the resultant reaction mixture to catalytic reduction to form 1-(4-hydroxyphenyl)-2-(4-benzylpiperidino)-1-propanol hydrobromide in the reaction mixture.

2. A process according to claim 1, wherein the hydrogen bromide formed in the course of the bromination is removed by fixing the hydrogen bromide as a salt with a basic substance in the reaction system.

3. A process according to claim 1, wherein the hydrogen bromide formed in the course of the bromination is removed by introducing an inert gas into the reaction system to expel the hydrogen bromide therefrom together with the inert gas.

4. A process according to claim 2, wherein the basic substance is selected from potassium hydrogen carbonate, sodium hydrogen carbonate, potassium carbonate, sodium carbonate, sodium acetate, triethylamine and 4-benzylpyridine.

5. A process according to claim 2, wherein the step of removing the hydrogen bromide formed in the course of the bromination by fixing the hydrogen bromide as a salt with the basic substance is carried out simultaneously with the step of adding 4-benzylpyridine to the reaction mixture.

6. A process according to claim 1, wherein the catalytic reduction is carried out by the aid of palladium-carbon at an elevated temperature under pressure.

7. A process according to claim 1, wherein the catalytic reduction is carried out by the aid of platinum oxide at room temperature under atmospheric pressure.

8. A process according to claim 1, wherein the saturated aliphatic ether is selected from diethyl ether, di-n-propyl ether, di-n-butyl ether, dioxane and tetrahydrofuran.

9. A process according to claim 1, wherein dioxane is used as the saturated aliphatic ether solvent in an amount of 0.6–1.0 part by volume per part by weight of the 4'-hydroxypropiophenone.

10. A process according to claim 1, wherein the brominating agent is bromine.

11. A process for the preparation of 1-(4-hydroxyphenyl)-2-(4-benzylpiperidino)-1-propanol and acid-addition salts thereof in a single reaction container, which comprises brominating 4'-hydroxypropriophenone in a single or mixed solvent selected from the group consisting of methanol, ethanol and dioxane, removing hydrogen bromide formed in the course of the bromination, adding 4-benzylpyridine and a single or mixed solvent selected from the group consisting of methanol and ethanol to the reaction mixture, heating the obtained reaction mixture under reflux and then subjecting the resultant reaction mixture to catalytic reduction to form 1-(4-hydroxyphenyl)-2-(4-benzylpiperidino)-1-propanol hydrobromide.

12. A process according to claim 11, wherein the hydrogen bromide formed in the course of the bromination is removed by fixing the hydrogen bromide as a salt with a basic substance in the reaction system.

13. A process according to claim 11, wherein the hydrogen bromide formed in the course of the bromination is removed by introducing an inert gas into the reaction system to expel the hydrogen bromide therefrom together with the inert gas.

14. A process according to claim 12, wherein the basic substance is selected from potassium hydrogen carbonate, sodium hydrogen carbonate, potassium carbonate, sodium carbonate, sodium acetate, triethylamine and 4-benzylpyridine.

15. A process according to claim 12, wherein the step of removing the hydrogen bromide formed in the course of the bromination by fixing the hydrogen bromide as a salt with the basic substance is carried out simultaneously with the step of adding 4-benzylpyridine to the reaction mixture.

16. A process according to claim 11, wherein the catalytic reduction is carried out by the aid of palladium-carbon at an elevated temperature under pressure.

17. A process according to claim 11, wherein the catalytic reduction is carried out by the aid of platinum oxide at room temperature under atmospheric pressure.

* * * * *